US012629046B2

(12) United States Patent
Kim et al.

(10) Patent No.: US 12,629,046 B2
(45) Date of Patent: May 19, 2026

(54) ELECTRONIC APPARATUS AND CONTROL METHOD THEREOF

(71) Applicants: SAMSUNG ELECTRONICS CO., LTD., Suwon-si (KR); INDUSTRY ACADEMIC COOPERATION FOUNDATION KEIMYUNG UNIVERSITY, Daegu (KR)

(72) Inventors: Doyoon Kim, Suwon-si (KR); Jongha Lee, Daegu (KR); Hyunsoo An, Suwon-si (KR); Chanil Kim, Daegu (KR); Eunbin Park, Daegu (KR)

(73) Assignees: SAMSUNG ELECTRONICS CO., LTD., Gyeonggi-Do (KR); INDUSTRY ACADEMIC COOPERATION FOUNDATION KEIMYUNG UNIVERSITY, Dalseo-Gu (KR)

( * ) Notice: Subject to any disclaimer, the term of this patent is extended or adjusted under 35 U.S.C. 154(b) by 810 days.

(21) Appl. No.: 17/897,017

(22) Filed: Aug. 26, 2022

(65) Prior Publication Data

US 2023/0078416 A1 Mar. 16, 2023

Related U.S. Application Data

(63) Continuation of application No. PCT/KR2022/012396, filed on Aug. 19, 2022.

(30) Foreign Application Priority Data

Sep. 16, 2021 (KR) ........................ 10-2021-0124082
Aug. 8, 2022 (KR) ........................ 10-2022-0098626

(51) Int. Cl.
$A61B\ 5/0537$ (2021.01)
$A61B\ 5/00$ (2006.01)

(52) U.S. Cl.
CPC ............ *A61B 5/0537* (2013.01); *A61B 5/486* (2013.01); *A61B 5/742* (2013.01)

(58) Field of Classification Search
None
See application file for complete search history.

(56) References Cited

U.S. PATENT DOCUMENTS 5,449,000 A * 9/1995 Libke ................... A61B 5/4872
600/547
11,540,739 B2 1/2023 Zhu et al.
(Continued)

FOREIGN PATENT DOCUMENTS

KR 101690425 B1 12/2016
KR 20170143256 A 12/2017
(Continued)

OTHER PUBLICATIONS

English Translation of KR20170143256 (Year: 2017).*
(Continued)

*Primary Examiner* — Adam J Eiseman
*Assistant Examiner* — Nelson Alexander Glover
(74) *Attorney, Agent, or Firm* — CANTOR COLBURN LLP

(57) ABSTRACT

Disclosed herein is an electronic apparatus. The electronic apparatus includes an electrode sensor configured to apply a current to an object and configured to measure an impedance of the object, a frequency controller configured to adjust a frequency of the applied current, a memory storing a correlation between an impedance and a vitamin D concentration for each frequency, and a processor configured to obtain the impedance of the object corresponding to the frequency, and to calculate a vitamin D concentration of the object based on the impedance and the correlation.

13 Claims, 21 Drawing Sheets

(56)         References Cited

U.S. PATENT DOCUMENTS

| | | | | |
|---|---|---|---|---|
| 2005/0039763 A1* | 2/2005 | Kraemer | ............. | A61B 5/0537 |
| | | | | 128/920 |
| 2005/0197555 A1* | 9/2005 | Mouradian | ........ | A61B 5/14532 |
| | | | | 600/365 |
| 2010/0087750 A1* | 4/2010 | McGree | ................ | A61B 5/053 |
| | | | | 600/547 |
| 2021/0148938 A1* | 5/2021 | Ninomiya | ............ | A61B 5/7275 |

FOREIGN PATENT DOCUMENTS

| | | | |
|---|---|---|---|
| KR | 20180003602 | A | 1/2018 |
| KR | 102035170 | B1 | 10/2019 |
| KR | 20190132962 | A | 11/2019 |
| KR | 102068587 | B1 | 1/2020 |
| KR | 20200110112 | A | 9/2020 |
| KR | 20210105945 | A | 8/2021 |

OTHER PUBLICATIONS

English Translation of KR20190132962 (Year: 2019).*
English Translation of KR102035170 (Year: 2019).*
International Search Report for International Application No. PCT/KR2022/012396; International Filing Date Aug. 19, 2022; Date of Mailing Dec. 14, 2022; 11 Pages.
Kim et al., Impedance Based Vitamin D Measurement Sensor and Algorithm for Human Wellness. Sensors & Transducers, 2017, vol. 2016, No. 9 and 10, pp. 1 to 7, pp. 3 to 6; Table 1.
Extended European Search Report Issued In EP Application No. 22870156.1-1113, Mail Date Nov. 6, 2024, 8 Pages.
European Office Action Issued In EP Patent Application No. 22 870 156.1-1113, Issue Date Aug. 6, 2025, 6 Pages.

* cited by examiner

FIRST CHARACTERISTIC FREQUENCY

SECOND CHARACTERISTIC FREQUENCY

Vitamin D (ng/mL)

$R^2 = 0.7564$ impedance($\Omega$)

THIRD CHARACTERISTIC FREQUENCY

Vitamin D (ng/mL)

impedance($\Omega$)

TABLE 1

SUMMARY · OF · THE · REGRESSION · MODEL · FOR · INBODY · MEASUREMENTS

| R2 | F–statistics | DOF · (Residuals) | DOF · (Model) | P–value | AIC | BIC |
|----|----|----|----|----|----|----|
| 0.196 | 2.803 | 23 | 2 | 0.0814 | 27.91 | 31.68 |

DOF · (Residuals) : Value · of · all · observed · variables · minus · the · number · of · variablesl · considered · in · the · regression · model DOF · (Model) : Number · of · variables · considered · in · the · regression · model

FIG. 8

TABLE 2

REGRESSION · MODEL · COEFFICIENTS · FOR · INBODY · MEASUREMENTS

| | Coefficient | Standardized · Error | T | P> \| t \| | 95% · CI | VIF | RMSE |
|---|---|---|---|---|---|---|---|
| Constant | -15.1132 | 8.909 | -1.696 | 0.103 | [-33.543, 3.317] | | |
| Right · leg · (muscle · analysis · by · part) | 3.817 | 1.875 | 2.036 | 0.053 | [-0.062, 7.696] | 2.8201 | 0.3688 |
| Body · fat · percentage | 0.0385 | 0.016 | 2.355 | 0.027 | [0.005, 0.072] | 2.8201 | |

TABLE 3

SUMMARY · OF · THE · REGRESSION · MODEL · FOR · BLOOD · ANALYSIS · PARAMETERS

| R2 | F-statistics | DOF · (Residuals) | DOF · (Model) | P-value | AIC | BIC |
|---|---|---|---|---|---|---|
| 0.714 | 9.981 | 20 | 5 | 6.64e-05 | 7.044 | 14.59 |

DOF · (Residuals) : Value · of · all · observed · variables · minus · the · number · of · variablesl · considered · in · the · regression · model DOF · (Model) : Number · of · variables · considered · in · the · regression · model

FIG. 13

TABLE 4

REGRESSION · MODEL · COEFFICIENTS · FOR · BLOOD · ANALYSIS · PARAMETERS

| | Coefficient | Standardized · Error | t | P> \|t\| | 95% · CI | VIF | RMSE |
|---|---|---|---|---|---|---|---|
| Constant | -2.4515 | 1.735 | -1.413 | 0.173 | [-6.07, 1.167] | | |
| Basophils | -0.9072 | 0.19 | -4.765 | 0.000** | [-1.304, -0.51] | 1.064 | |
| Albumin | 1.3068 | 0.317 | 4.116 | 0.001** | [0.645, 1.969] | 1.1865 | 0.2199 |
| Female | 0.5616 | 0.126 | 4.447 | 0.000** | [0.298, 0.825] | 1.6381 | |
| MDRD | -0.0087 | 0.004 | -2.38 | 0.027* | [-0.016, -0.001] | 1.5744 | |
| LDH | 0.0021 | 0.001 | 2.239 | 0.037* | [0.000, 0.004] | 1.1857 | |

*p<.05, **p<.005

Pesidual

Predict

TABLE 5

SUMMARY · OF · THE · REGRESSION · MODEL · FOR
· SKIN · IMPEDANCE · MEASUREMENTS

| R2 | F-statistics | DOF · (Residuals) | DOF · (Model) | P-value | AIC | BIC |
|---|---|---|---|---|---|---|
| 0.159 | 4.543 | 24 | 1 | 0.0435 | 27.07 | 29.59 |

DOF · (Residuals) : Value · of · all · observed · variables · minus · the · number · of · variablesl · considered · in · the · regression · model DOF · (Model) : Number · of · variables · considered · in · the · regression · model

FIG. 18

TABLE 6

REGRESSION · MODEL · COEFFICIENTS · FOR · SKIN · IMPEDANCE · MEASUREMENTS

| | Coefficient | Standardized · Error | t | P> \| t \| | 95% · CI | VIF | RMSE |
|---|---|---|---|---|---|---|---|
| Constant | -4.2907 | 3.57 | -1.202 | 0.241 | [-11.659, 3.078] | | 0.3771 |
| 21.1 · Hz | 0.4419 | 0.207 | 2.131 | 0.043 | [0.014, 0.87] | 1 | |

*p<.05

ELECTRONIC APPARATUS AND CONTROL METHOD THEREOF

CROSS-REFERENCE TO RELATED APPLICATION(S)

This application is a continuation application, under 35 U.S.C. § 111(a), of international application No. PCT/KR2022/012396, filed on Aug. 19, 2022, which claims priority to Korean Patent Application Nos. 10-2022-0098626, filed on Aug. 8, 2022 and 10-2021-0124082, filed on Sep. 16, 2021, in the Korean Intellectual Property Office, the disclosure of which is incorporated by reference herein in its entirety

BACKGROUND

1. Field

The disclosure relates to an electronic apparatus capable of measuring a vitamin D concentration in a body and a control method thereof.

2. Description of Related Art

Vitamin D is an essential nutrient and plays an essential role in the musculoskeletal system. Insufficient vitamin D levels cause rickets in children and osteomalacia, bone pain and muscle weakness in adults. Excessive levels of vitamin D can cause vomiting, muscle weakness, confusion, pain, loss of appetite, dehydration, excessive urination, thirst, and kidney stones.

For measuring of a vitamin D level in the body, there is a method of quantitatively measuring a vitamin D level in serum, but it is inconvenience in terms of cost as well as an invasive process.

In recent years, a device for measuring a state of the body by measuring an impedance of the body have been developed in various fields. However, the device does not consider various factors and thus there is an inaccuracy in a quantitative aspect.

SUMMARY

Therefore, it is an aspect of the disclosure to provide an electronic apparatus capable of accurately measuring a vitamin D level in a body based on an impedance and biometric information related to vitamin D, and a control method thereof.

Additional aspects of the disclosure will be set forth in part in the description which follows and, in part, will be obvious from the description, or may be learned by practice of the disclosure.

In accordance with an aspect of the disclosure, an electronic apparatus includes an electrode sensor configured to apply a current to an object and configured to measure an impedance of the object, a frequency controller configured to control a frequency of the applied current, a memory storing a correlation between impedance and vitamin D concentration for the frequency, and a processor configured to obtain an impedance of the object corresponding to the frequency, and calculate a vitamin D concentration of the object based on the correlation.

The memory may store a parameter corresponding to a biometric information related to the object, and the processor may be configured to calculate a final vitamin D concentration by applying the parameter to the vitamin D concentration.

The memory may store a correlation between the impedance and the vitamin D concentration for each of a plurality of frequencies.

The frequency controller may be configured to set a frequency of the applied current to be output as one of a first characteristic frequency, a second characteristic frequency, and a third characteristic frequency.

The frequency controller may be configured to sequentially output the first characteristic frequency, the second characteristic frequency, and the third characteristic frequency.

The electrode sensor may include a first electrode and a second electrode arranged on a rear surface of a main body of the electronic apparatus and in direct contact with the object, and the electrode sensor may be configured to apply a current through one of the first electrode or the second electrode and configured to measure a voltage between the first electrode and the second electrode so as to measure an impedance.

The biometric information may include physical health information, and the physical health information may include at least one of user's gender, age, height, weight, body mass index (BMI), blood pressure level, white blood cell count, lipid level, liver level, and glucose level.

The biometric information may include bio-signal measurements, and the bio-signal measurements may include at least one of skeletal muscle mass, body fat mass, body fat percentage, body mass index (BMI), body water, and basal metabolic rate.

The biometric information may include blood analysis information, and the blood analysis information may include at least one of hemoglobin, fasting blood sugar, total cholesterol, HDL-cholesterol, triglyceride level, LDL-cholesterol, serum creatinine, AST, ALT, and r-GTP.

The electronic apparatus may further include an input device configured to receive the biometric information from a user and a display provided to display a vitamin D concentration. In response to the biometric information being input through the input device, the processor may be configured to control the display to output the final vitamin D concentration to which the parameter is applied.

In response to the output of the final vitamin D concentration, the processor may be configured to control the display to provide a nutrition guide corresponding to the final vitamin D concentration.

In accordance with another aspect of the disclosure, a control method of an electronic apparatus including a memory storing a correlation between an impedance and a vitamin D concentration for multiple frequencies, the control method includes applying a current to an object and measuring an impedance of the object, adjusting a frequency of the applied current, and obtaining the impedance of the object while the frequency is varied, determining the a correlation to which the obtained impedance belongs, and calculating a vitamin D concentration of the object based on the correlation.

The memory may store a parameter corresponding to a biometric information related to the object. The calculation of the vitamin D concentration of the object may include calculating a final vitamin D concentration by applying the parameter to the vitamin D concentration.

The memory may store a correlation between the impedance and the vitamin D concentration for each characteristic frequency.

The adjustment of the frequency of the applied current may include outputting a frequency of the applied current as one of a first characteristic frequency, a second characteristic frequency, and a third characteristic frequency.

The adjustment of the frequency of the applied current may include sequentially outputting the first characteristic frequency, the second characteristic frequency, and the third characteristic frequency.

The electronic apparatus may include an electrode sensor including a first electrode and a second electrode arranged on a rear surface of a main body of the electronic apparatus and in direct contact with the object, the electrode sensor configured to apply a current through one of the first electrode or the second electrode and configured to measure a voltage between the first electrode and the second electrode so as to measure an impedance.

The biometric information may include physical health information, and the physical health information may include at least one of user's gender, age, height, weight, body mass index (BMI), blood pressure level, white blood cell count, lipid level, liver level, and glucose level.

The biometric information may include bio-signal measurements, and the bio-signal measurements may include at least one of skeletal muscle mass, body fat mass, body fat percentage, body mass index (BMI), body water, and basal metabolic rate.

The biometric information may include blood analysis information, and the blood analysis information may include at least one of hemoglobin, fasting blood sugar, total cholesterol, HDL-cholesterol, triglyceride level, LDL-cholesterol, serum creatinine, AST, ALT, and r-GTP.

BRIEF DESCRIPTION OF THE DRAWINGS

These and/or other aspects of the disclosure will become apparent and more readily appreciated from the following description of embodiments, taken in conjunction with the accompanying drawings of which:

FIG. 7 is a table illustrating summary of a regression model for In-Body measurements;

FIG. 8 is a table summarizing regression model coefficients for In-Body measurements;

FIG. 12 is a table illustrating summary of a regression model for blood analysis parameters;

FIG. 13 is a table summarizing regression model coefficients for blood analysis parameters;

FIG. 15 is a graph illustrating a Q-Q plot of residuals for hematology items;

FIG. 17 is a table illustrating summary of regression model for skin impedance measurements;

FIG. 18 is a table summarizing regression model coefficients for skin impedance measurements;

DETAILED DESCRIPTION

Figure 1:
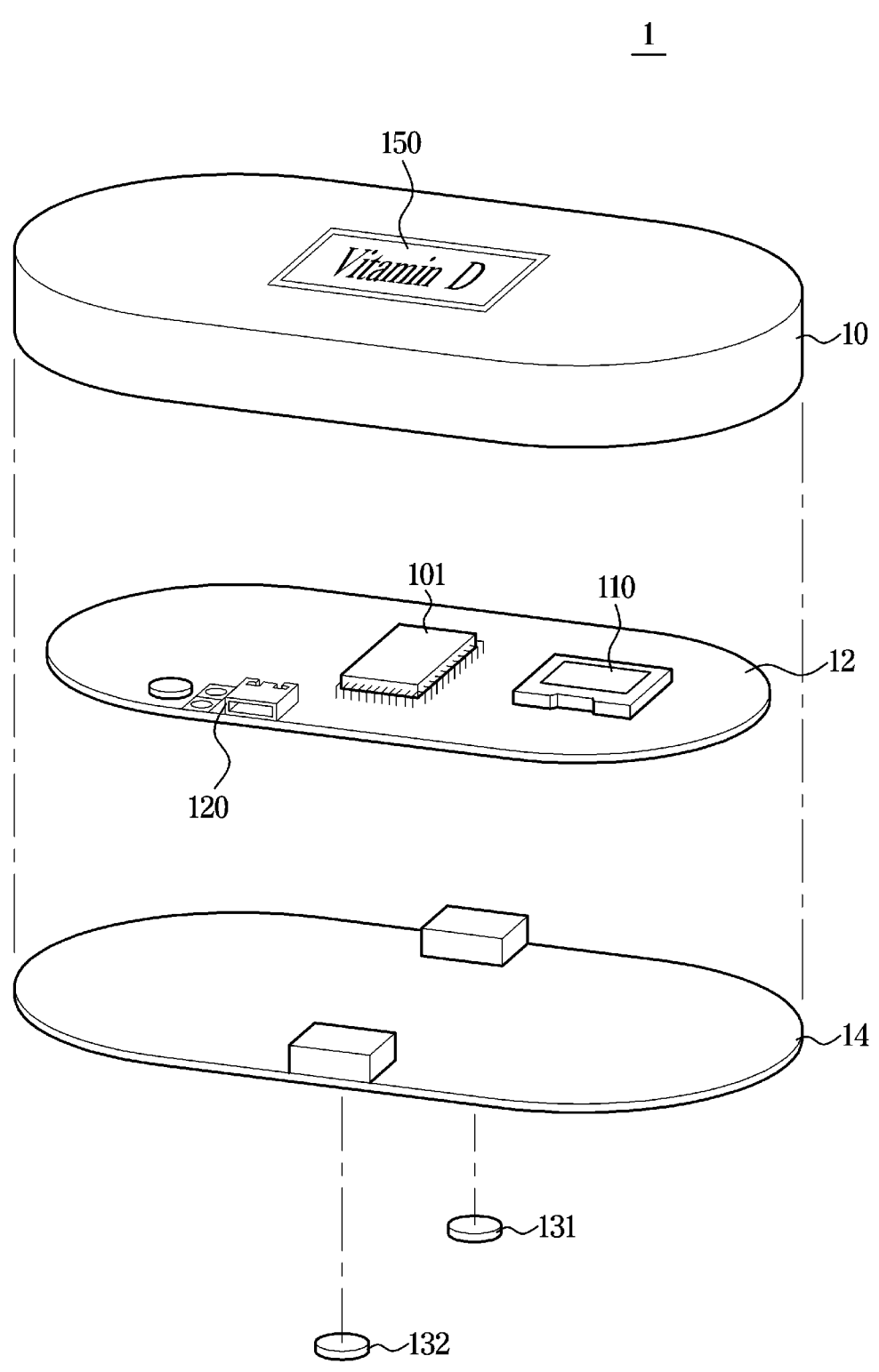
FIG. 1 is a view illustrating a schematic diagram of an electronic apparatus according to an embodiment of the disclosure.

In the following description, like reference numerals refer to like elements throughout the specification. Well-known functions or constructions are not described in detail since they would obscure the one or more exemplar embodiments with unnecessary detail. Terms such as "unit", "module", "member", and "block" may be embodied as hardware or software. According to embodiments, a plurality of "unit", "module", "member", and "block" may be implemented as a single component or a single "unit", "module", "member", and "block" may include a plurality of components.

It will be understood that when an element is referred to as being "connected" another element, it can be directly or indirectly connected to the other element, wherein the indirect connection includes "connection via a wireless communication network".

Also, when a part "includes" or "comprises" an element, unless there is a particular description contrary thereto, the part may further include other elements, not excluding the other elements.

Throughout the description, when a member is "on" another member, this includes not only when the member is in contact with the other member, but also when there is another member between the two members.

It will be understood that, although the terms first, second, third, etc., may be used herein to describe various elements, but is should not be limited by these terms. These terms are only used to distinguish one element from another element.

As used herein, the singular forms "a," "an" and "the" are intended to include the plural forms as well, unless the context clearly indicates otherwise.

An identification code is used for the convenience of the description but is not intended to illustrate the order of each step. The each step may be implemented in the order different from the illustrated order unless the context clearly indicates otherwise.

Reference will now be made in detail to embodiments of the disclosure, examples of which are illustrated in the accompanying drawings.

Figure 2:
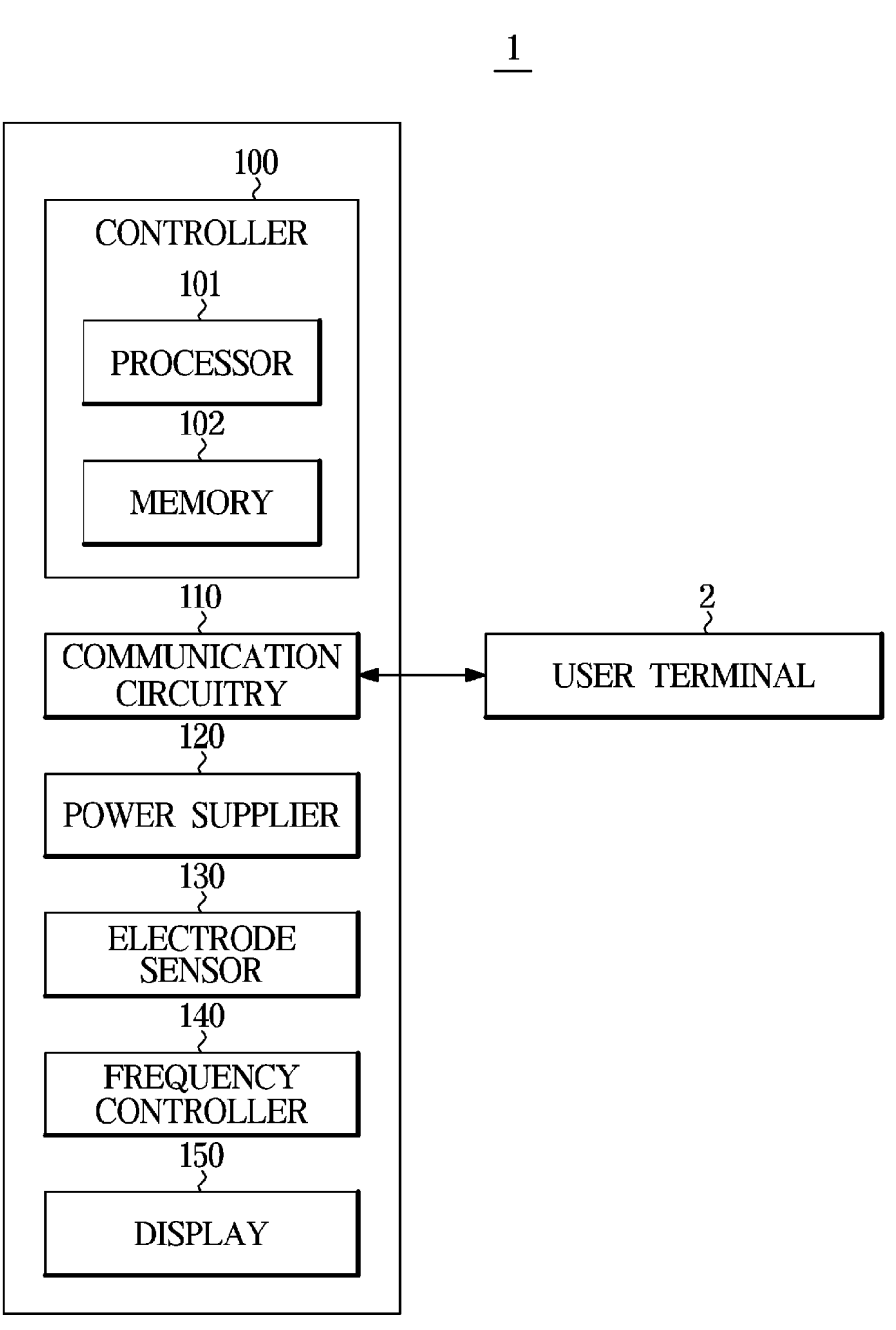
FIG. 2 is a block diagram illustrating the electronic apparatus according to an embodiment of the disclosure.

FIG. 1 is a view illustrating a schematic diagram of an electronic apparatus according to an embodiment of the disclosure, and FIG. 2 is a block diagram illustrating the electronic apparatus according to an embodiment of the disclosure.

An electronic apparatus 1 may form a main body by a first case 10 corresponding an upper portion and a second case 14 corresponding a lower portion. A substrate 12 to which various elements for an operation of the electronic apparatus 1 are mounted may be arranged between the first case 10 and the second case 14. A processor 101, a communication circuitry 110 and a power supplier 120 may be mounted to the substrate 12 corresponding to a printed circuit board (PCB).

The electronic apparatus 1 shown in FIG. 1 is in the form of a portable device that a user carries separately, but the electronic apparatus 1 may be implemented in the form of a smart watch that is a wearable device that is configured to be directly mounted on the user's body and used.

A display 150 may be provided on a surface of the first case 10, and the display 150 may output various information obtained through the electronic apparatus 1. In response to a current applied to a part of the user's body from a first electrode 131 or a second electrode 132, a controller 100 may measure an impedance. In exemplary embodiments, the controller 100 controls the display 150 to output the measured impedance and a vitamin D concentration obtained through an algorithm described in more detail below.

The first electrode 131 and the second electrode 132 are configured to come into contact with the user's skin and may be arranged on a surface of the second case 14. The first electrode 131 and the second electrode 132 may apply a micro-current to the user's skin to measure a voltage between the first electrode 131 and the second electrode, thereby measuring an impedance.

The controller 100 may include a memory 102 storing programs and data, and a processor 101 configured to process data according to the program stored in the memory 102 and configured to control the communication circuitry 110, a frequency controller 140 and the display 150.

The memory 102 may store a control program and control data for controlling the operation of the electronic apparatus 1, and a correlation between an impedance and a vitamin D concentration for multiple different frequencies.

Further, the memory 102 may store various pieces of biometric information that is input by the user through the electronic apparatus 1.

For example, the biometric information may include physical health information such as user's gender, age, height, weight, body mass index (BMI), blood pressure level, white blood cell count, lipid level, liver level, and glucose level, and bio-signal measurements such as skeletal muscle mass, body fat mass, body fat percentage, body mass index (BMI), body water, and basal metabolic rate. In addition, the biometric information may include blood analysis information such as hemoglobin, fasting blood sugar, total cholesterol, HDL-cholesterol, triglyceride level, LDL-cholesterol, serum creatinine, AST, ALT, and r-GTP.

The memory 102 may include a volatile memory such as static random access memory (S-RAM), and dynamic random access memory (D-RAM), and a nonvolatile memory such as read only memory (ROM), erasable programmable read only memory (EPROM), electrically erasable programmable read only memory (EEPROM), and flash memory.

The communication circuitry 110 may include a short-distance communication module for exchanging data with a user terminal 2. The communication circuitry 110 may communicate with a communication target in various communication methods. For example, a short-range communication module may communicate with a communication target using a Wi-Fi communication method (IEEE 802.11), a Bluetooth communication method (IEEE 802.15.1), a Zigbee communication method (IEEE 802.15.4), or the like. However, the short-distance communication module does not employ all of the Wi-Fi communication method, the Bluetooth communication method, and the Zigbee communication method, but the short-distance communication module may employ at least one of the Wi-Fi communication method, the Bluetooth communication method, and the Zigbee communication method.

The user terminal 2 may store various application programs and data that perform various functions according to a user input. For example, the user terminal 2 may receive biometric information from the user, and may derive a final vitamin D concentration by applying a parameter corresponding to the biometric information to the vitamin D concentration derived by the electronic apparatus 1.

The power supplier 120 may include a battery or dry cell configured to charge and discharge, and the power supplier 120 may be configured to supply driving power to the electronic apparatus 1 through battery power or dry-cell power. The driving power supplied from the power supplier 120 may cause an electrode sensor 130 to generate a micro-AC current.

By using the driving power supplied from the power supplier 120, the electrode sensor 130 may allow a micro-current to flow in a part of the user's body. The electrode sensor 130 may include the first electrode 131 and the second electrode 132 which are in direct contact with an object (user's body). The electrode sensor 130 may apply a micro-current through one of the first electrode 131 and the second electrode 132, and measure a voltage between the first electrode 131 and the second electrode 132, thereby measuring an impedance.

The electrode sensor 130 may include a current detection circuit (not shown) configured to detect a micro-current passing through the user's body. For example, the electrode sensor 130 may apply a micro-current from one point of an object to another point of the object, and measure the applied micro-current (current flowing through the body) and a potential difference between two points in a path through which the current flows, thereby measuring a bio-impedance of a user.

The frequency controller 140 may vary a frequency of the micro-current supplied from the electrode sensor 130. The micro-current supplied by the electrode sensor 130 may be an alternating current, and a magnitude and frequency of the current may be varied according to a control signal of the controller 100. For example, the frequency controller 140 controls the electrode sensor 130 to output a micro-current having a characteristic frequency. The characteristic frequency corresponds to a value experimentally selected as a frequency value at which the vitamin D concentration is optimally measured. The characteristic frequency will be described in detail with reference to FIGS. 3 to 5.

The display 150 may display various types of information obtained through the electronic apparatus 1. For example, the display 150 may display the impedance measured through the electrode sensor 130 and the vitamin D concentration obtained based on the impedance. The display 150 may be implemented as a touch screen module, and may receive a user's touch input and a command corresponding to the touch input, or may output information corresponding to the touch input.

In the above description, the physical configuration of the electronic apparatus 1 and operations of each configuration have been described. The electronic apparatus 1 according to the disclosure measures an impedance of an object based on a micro-current, and then measures a vitamin D concentration in a user's body based on the impedance. At this time, the vitamin D concentration may be derived by an algorithm according to the disclosure. Hereinafter the algorithm for estimating the vitamin D concentration will be described in detail.

Figure 3:
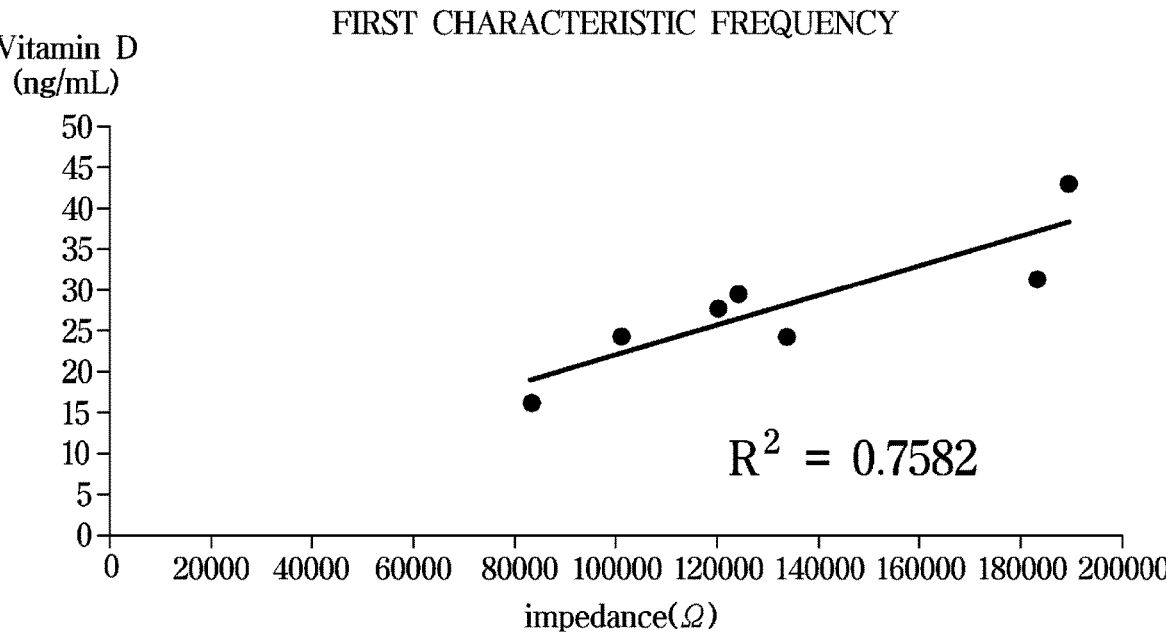
FIG. 3 is a graph illustrating a correlation between an impedance and a vitamin D concentration for each characteristic frequency.
Figure 4:
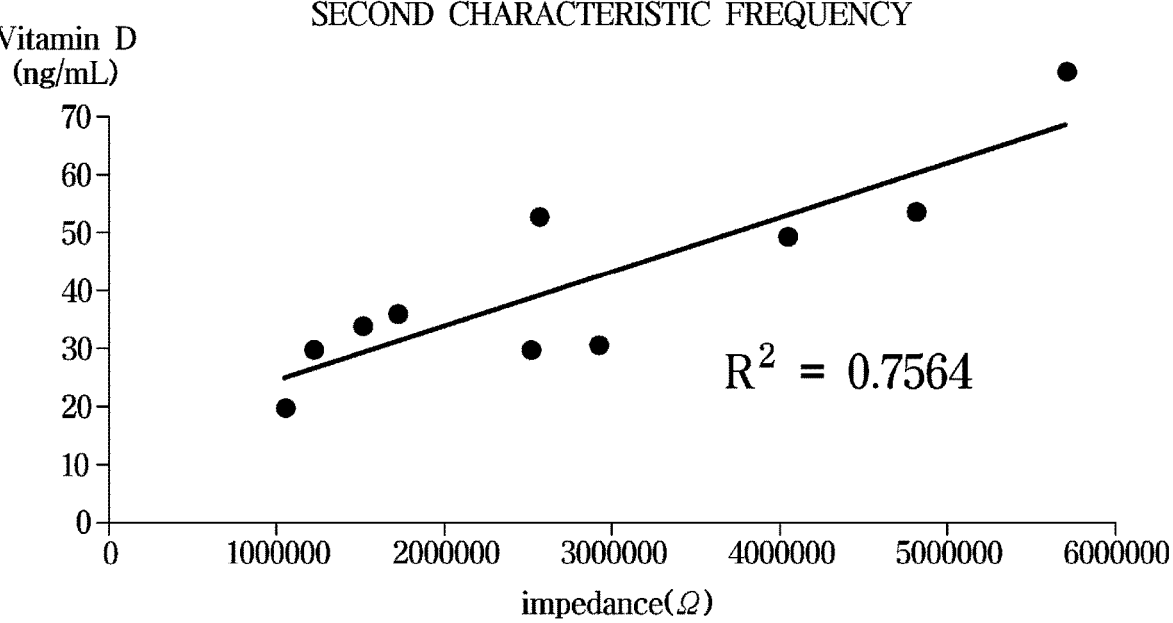
FIG. 4 is a graph illustrating a correlation between an impedance and a vitamin D concentration for each characteristic frequency.
Figure 5:
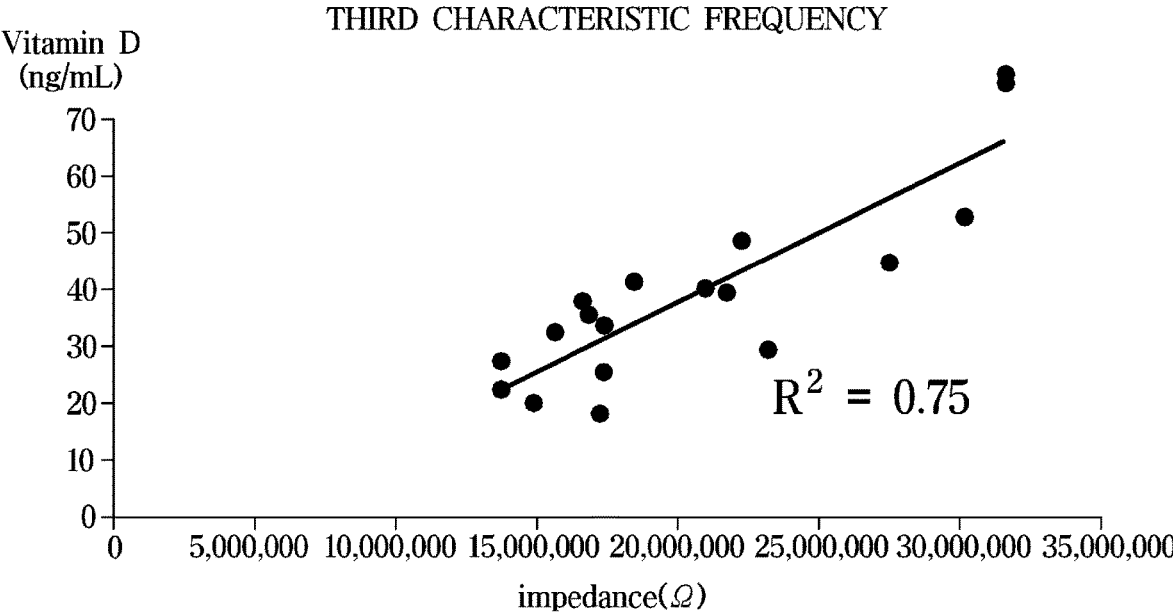
FIG. 5 is a graph illustrating a correlation between an impedance and a vitamin D concentration for each characteristic frequency.

FIGS. 3 to 5 are graphs illustrating a correlation between an impedance and a vitamin D concentration for each characteristic frequency.

The disclosure is for estimating a vitamin D concentration in a user's body using the electronic apparatus 1 configured to measure an impedance. For this, a correlation between a vitamin D concentration and an impedance is analyzed in advance, and a characteristic frequency that minimizes a difference between a vitamin D concentration actually measured in the body and a vitamin D concentration estimated based on the impedance is used through the normality test performed in advance.

FIGS. 3 to 5 illustrate a correlation between an impedance and a vitamin D concentration at a first characteristic frequency, a second characteristic frequency, and a third characteristic frequency, respectively. The first characteristic frequency is 21.1 Hz, the second characteristic frequency is 22.2 Hz, and the third characteristic frequency is 23.4 Hz. In the normality test, the vitamin D concentration satisfies the normality at the first characteristic frequency to the third characteristic frequency.

In a model design, the first to third characteristic frequencies identified in the normality test are set as input variables, and a log value of vitamin D concentration is set as output variables. Variable selection criteria are analyzed by defining significance levels as 0.05 and 0.1, respectively, when selecting and removing factors.

Analysis of the correlation between the collected frequency information and the vitamin D concentration confirms that the impedance measurement frequency of 21.1 Hz (t=2.131, p<0.05) appears to have a statistically significant effect.

Using the characteristic frequency of 21.1 Hz among the collected frequencies, a correlation between the impedance values and the vitamin D concentration values confirmed through blood analysis is analyzed using a linear regression equation. In response to the application of a micro-current having the third characteristic frequency, a value of R2=0.75 is obtained for the regression equation, showing 75% of an explanatory power (FIG. 5).

Figure 6:
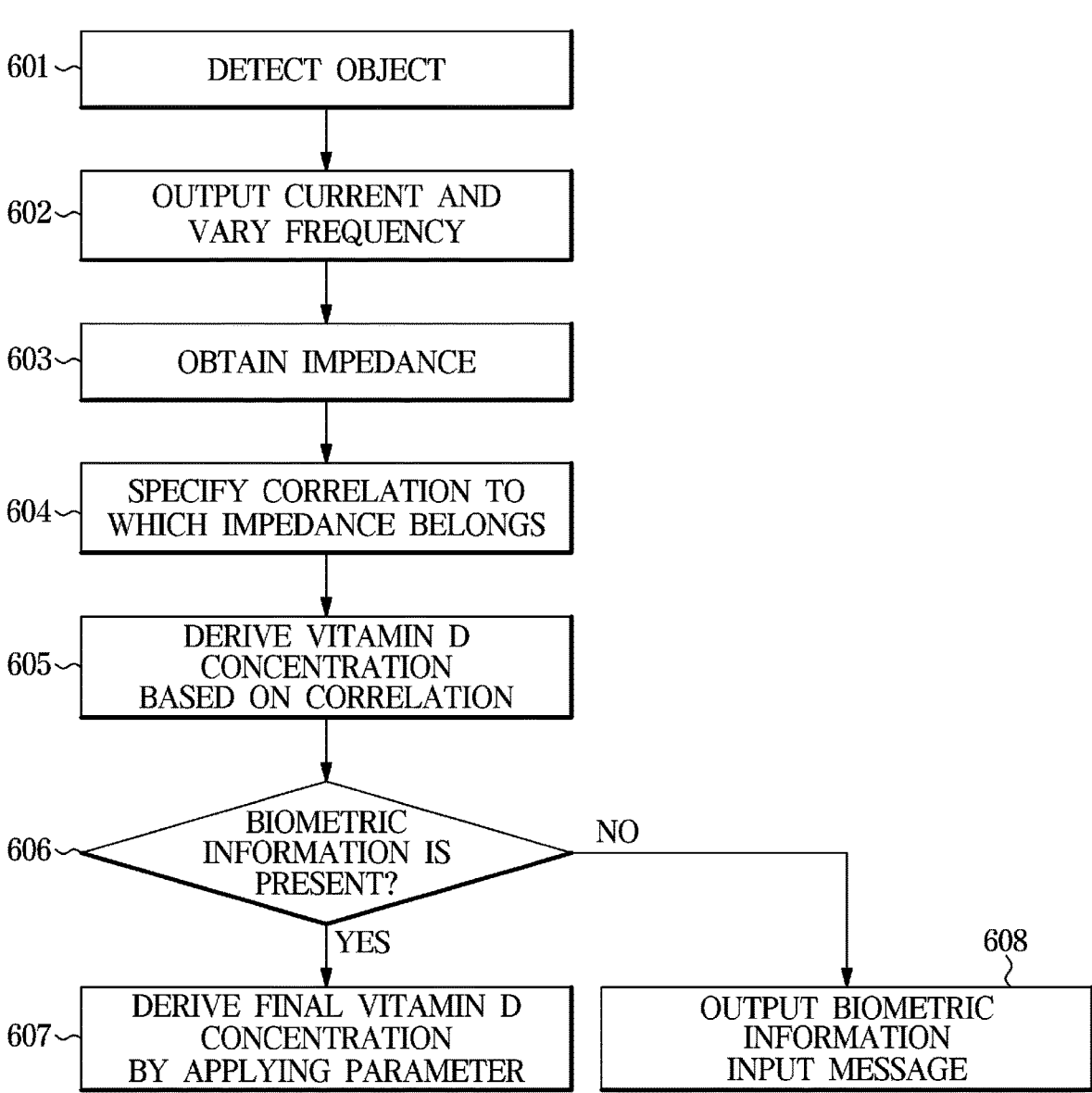
FIG. 6 is a flowchart illustrating a method for controlling the electronic apparatus according to an embodiment of the disclosure.

FIG. 6 is a flowchart illustrating a method for controlling the electronic apparatus according to an embodiment of the disclosure.

The electronic apparatus 1 detects an object (user's skin) through the electrode sensor 130, as shown at block 601.

In a state in which the electrode sensor 130 is in contact with the object, a current is output and a frequency thereof is varied, as shown at block 602. Through the frequency controller 140, the electronic apparatus 1 may vary the frequency of the micro-current supplied from the electrode sensor 130. The electronic apparatus 1 sets a frequency of the micro-current to be a characteristic frequency. The characteristic frequency is experimentally and statistically selected, and may be one of the first characteristic frequency (21.1 Hz), the second characteristic frequency (22.2 Hz), and the third characteristic frequency (23.4 Hz).

The frequency controller 140 according to an embodiment may output the frequency of the applied micro-current as one of the first characteristic frequency, the second characteristic frequency, and the third characteristic frequency, and may sequentially output the first characteristic frequency, the second characteristic frequency and the third characteristic frequency.

In one embodiment, the frequency controller 140 may cross-verify whether there is a difference between the vitamin D concentrations measured at each characteristic frequency. The difference between the three values may be determined by subtracting the smallest vitamin D concentration from the highest vitamin D concentration. In one embodiment, if the difference is above a threshold value, a composite vitamin D concentration may be determined by taking an average of the vitamin D concentrations measured at each characteristic frequency. In another embodiment, if the difference is above a threshold value, a composite vitamin D concentration may be determined by taking an average of the two vitamin D concentrations that have the closest values.

The electronic apparatus 1 obtains an impedance with respect to the micro-current, as shown at block 603, and specifies a correlation to which the impedance belongs, as shown at block 604. In this case, the correlation is stored for each characteristic frequency, and corresponds to the correlation between the impedance and the vitamin D concentration for each characteristic frequency.

For example, referring to FIG. 3, in response to the application of the micro-current having the first characteristic frequency to the object, an impedance of a specific value is measured. Accordingly, based on the correlation shown in FIG. 3, it is possible to derive a vitamin D concentration in the user's body.

The electronic apparatus 1 derives the vitamin D concentration based on the correlation, as shown at block 605.

The controller 100 according to an embodiment obtains the impedance of the object while varying the frequency of the micro-current, specifies a correlation to which the obtained impedance belongs, and calculates the vitamin D concentration of the object based on the correlation.

Basically, the electronic apparatus 1 calculates the vitamin D concentration based on the impedance value, but may re-estimate the measured vitamin D concentration based on one or more pieces of biometric information of the user. That is, the electronic apparatus 1 calculates a final vitamin D concentration by applying various parameters to the vitamin D concentration.

In response to the presence of biometric information previously input to the electronic apparatus 1, as shown at decision block 606, the electronic apparatus 1 derives the final vitamin D concentration by applying the stored parameters, as shown at block 607.

Conversely, in response to the absence of biometric information previously input to the electronic apparatus 1, the electronic apparatus 1 controls the display 150 to output a biometric information input message, as shown at block 608.

The electronic apparatus 1 according to an embodiment may further include an input device configured to receive the biometric information from the user and a display provided to display the vitamin D concentration. In response to the reception of the biometric information through the input device, the processor 101 may output the final vitamin D concentration to which the parameter is applied. In exemplary embodiments, the input device may be a display 150 or a user terminal 2 shown in FIG. 2.

In response to the output of the final vitamin D concentration, the electronic apparatus 1 according to an embodiment may control the display 150 to provide a nutrition guide corresponding to the final vitamin D concentration.

In exemplary embodiments, the electronic apparatus 1 may use the user's biometric information to derive the final vitamin D concentration. The electronic apparatus 1 may more accurately estimate the vitamin D concentration by additionally applying biometric information related to the vitamin D concentration. FIGS. 7 to 11 are measurement results in consideration of In-Body measurement values, and FIGS. 12 to 16 are measurement results in further consideration of blood information.

Figure 9:
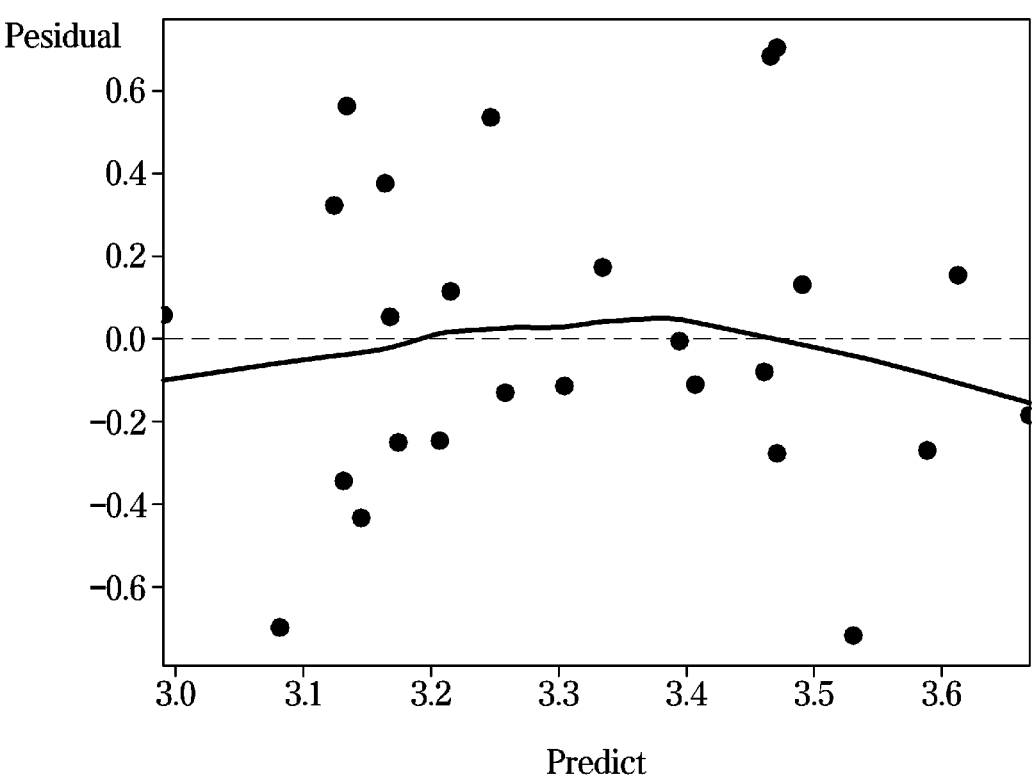
FIG. 9 is a graph illustrating a comparison between In-Body predicted values and residuals.
Figure 10:
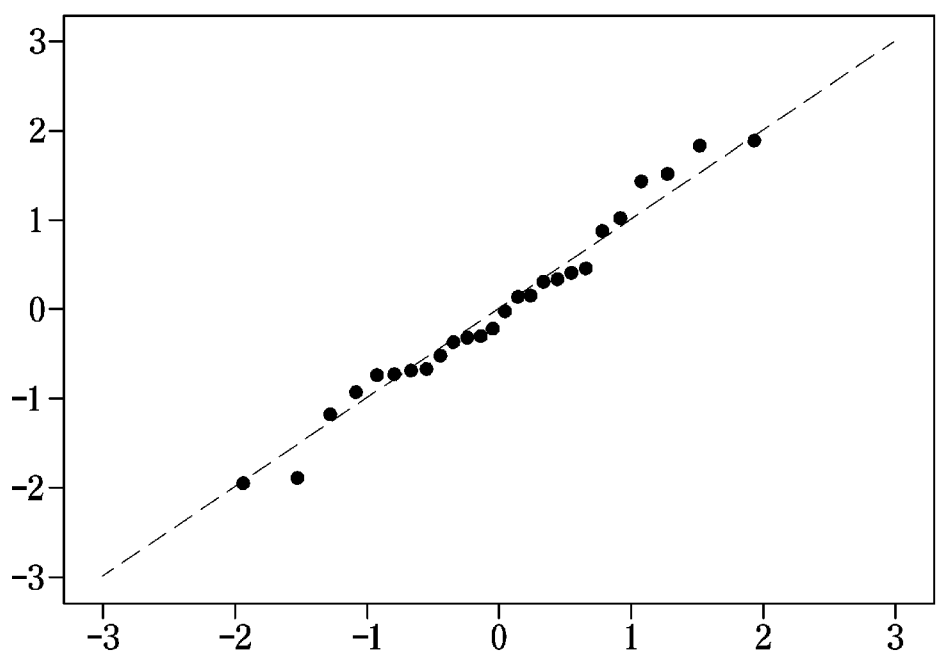
FIG. 10 is a graph illustrating a Q-Q plot of In-Body residuals.
Figure 11:
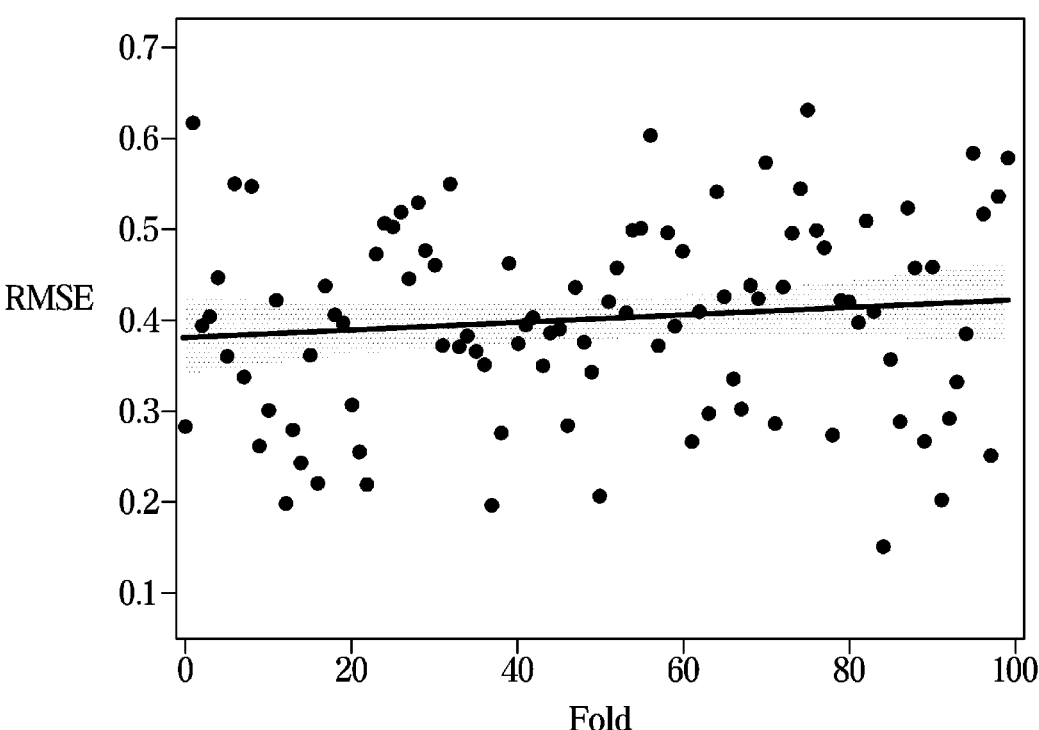
FIG. 11 is a graph illustrating root mean square errors for blood analysis parameters.

FIG. 7 is a table illustrating summary of a regression model for In-Body measurements. FIG. 8 is a table summarizing regression model coefficients for In-Body measurements. FIG. 9 is a graph illustrating a comparison between In-Body predicted values and residuals. FIG. 10 is a graph illustrating a Q-Q plot of In-Body residuals. FIG. 11 is a graph illustrating root mean square errors for blood analysis parameters.

Referring to FIG. 7, the F statistic of the regression model shows a level of 2.803 at p (probability value)=0.0814, and R2=0.196, which shows an explanatory power of 19.6%. Analysis of the relationship between the factors collected from an In-Body device and the vitamin D level indicates that the right leg and the body fat percentage have an effect on muscle analysis by part.

Referring to FIG. 8, body fat percentage (t=2.355, p<0.05) is found to have a statistically significant effect. FIG. 9 illustrates a comparison result between a predicted value (ŷ) and a residual (y-ŷ) in order to confirm the linearity of the model. The predicted value (log value) of vitamin D shows a larger error corresponding to values less than 3.1 and 3.65 or more. Shapiro-Wilk test performed to confirm the normality of the residuals shows that the normality is satisfied at a significance level of 5% with p=0.6226 (FIG. 10).

Statistical cross validation is performed by dividing all of the data into sub-data for training and validation (training: 80%, validation: 20%). An average root mean squared error (RMSE) and standard deviation for 100 trials using random seeds are estimated to be 0.4±0.1072. (FIG. 11).

Figure 14:
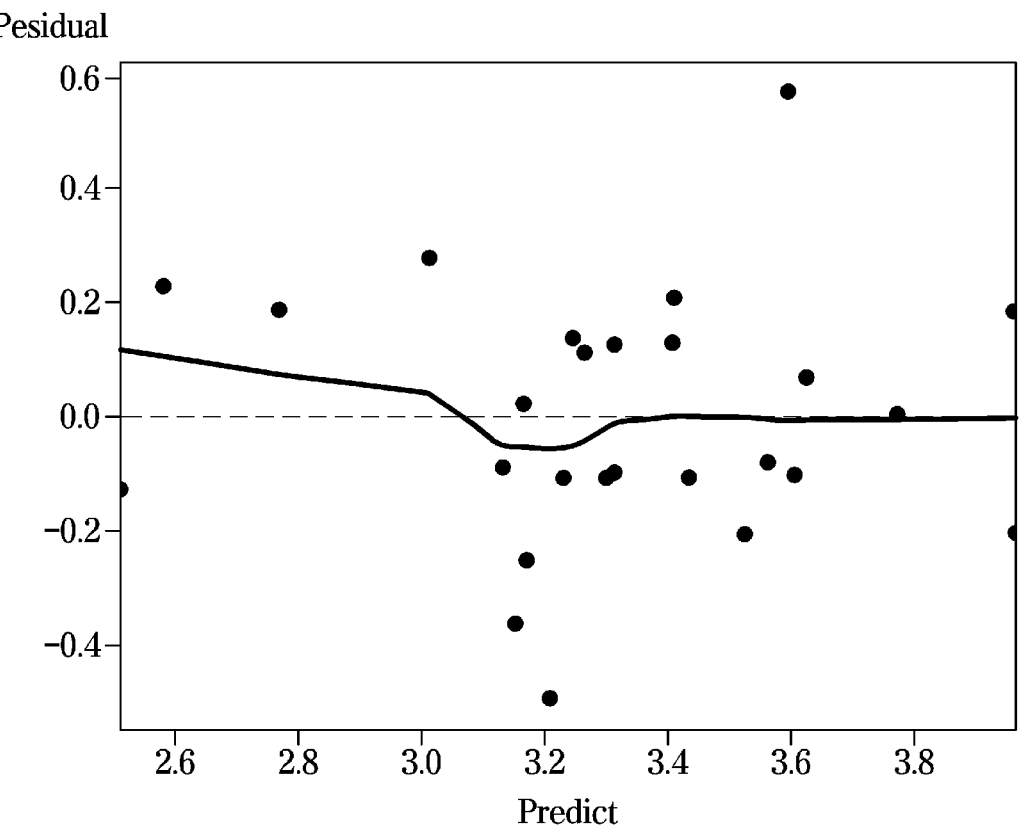
FIG. 14 is a graph illustrating a correlation between predictive values and residuals for blood analysis parameters.
Figure 15:
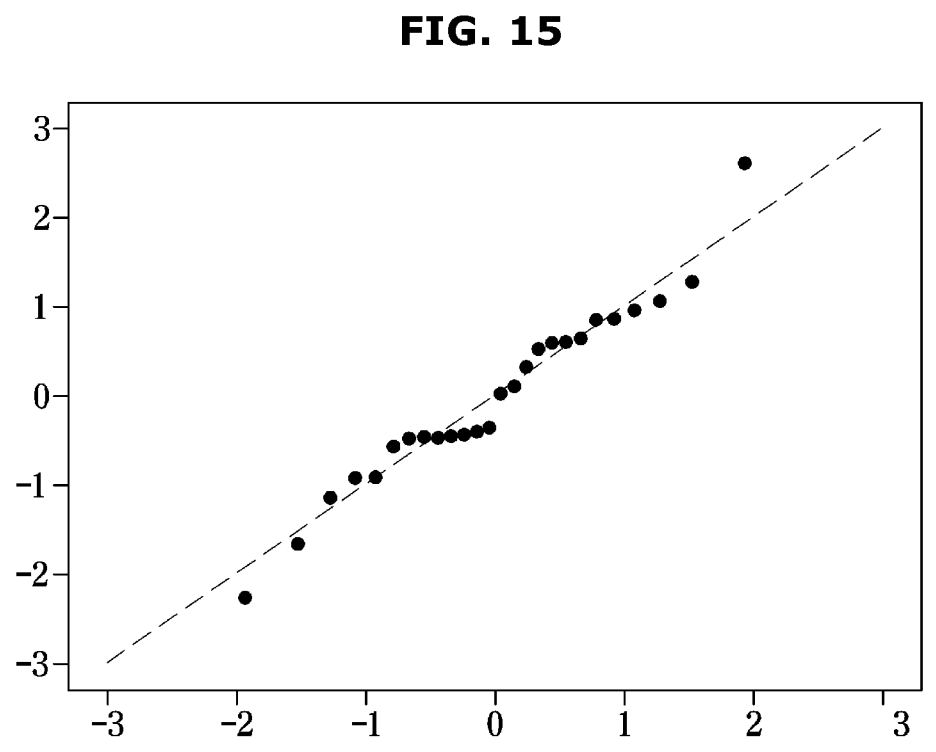
Figure 16:
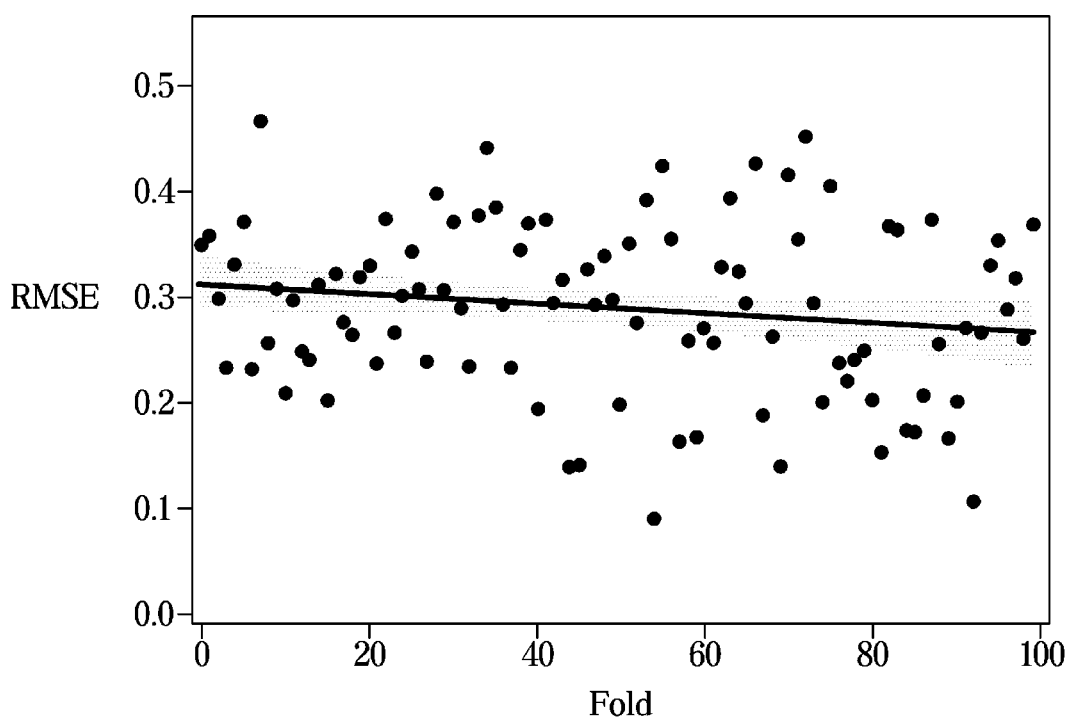
FIG. 16 is a graph illustrating root mean square errors for blood analysis parameters.

FIG. 12 is a table illustrating summary of a regression model for blood analysis parameters. FIG. 13 is a table summarizing regression model coefficients for blood analysis parameters, FIG. 14 is a graph illustrating a correlation between predictive values and residuals for blood analysis parameters, FIG. 15 is a graph illustrating a Q-Q plot of residuals for hematology items, and FIG. 16 is a graph illustrating root mean square errors for blood analysis parameters.

FIGS. 12 to 16 are a result of analysis of a correlation between a vitamin D level in the body and 50 variables such as physical measurement, blood pressure, general blood test, white blood cell test, lipid level, liver function test, glucose test, and kidney/pancreas/other tests for participants. It is possible to select blood analysis parameters so as to select measurement parameters that may be used to estimate vitamin D levels.

Referring to FIG. 12, the F statistic of the regression model shows a level of 9.981 at p=6.64e-05 and R2=0.714 for the regression formula, which shows an explanatory power of 71.4%.

Referring to FIG. 13, after the analysis of the association between the blood parameters and vitamin D, parameters such as female (t=4.447, p<0.005), basophils (t=−4.765, p<0.005), albumin (t=4.116, p<0.005), modification of diet in renal disease (MDRD) (t=−2.38, p<0.05), and LDH (t=2.239, p<0.05) are investigated, and the statistically significant effect is confirmed.

Referring to FIG. 14, as a result of comparing a predicted value (y) and a residual (y-ŷ) to confirm the linearity of the model, the predicted value (value) of vitamin D shows a larger error at values less than 3.38. Shapiro-Wilk test performed to confirm the normality of the residuals shows that the normality is satisfied at a significance level of 5% with p=0.6646 (FIG. 15).

Statistical cross validation is performed by dividing the entire data into sub-data for training and validation (training: 80%, validation: 20%), and an average root mean squared error (RMSE) and standard deviation using a random seed are estimated to be 0.2896±0.0807 (FIG. 16).

Figure 19:
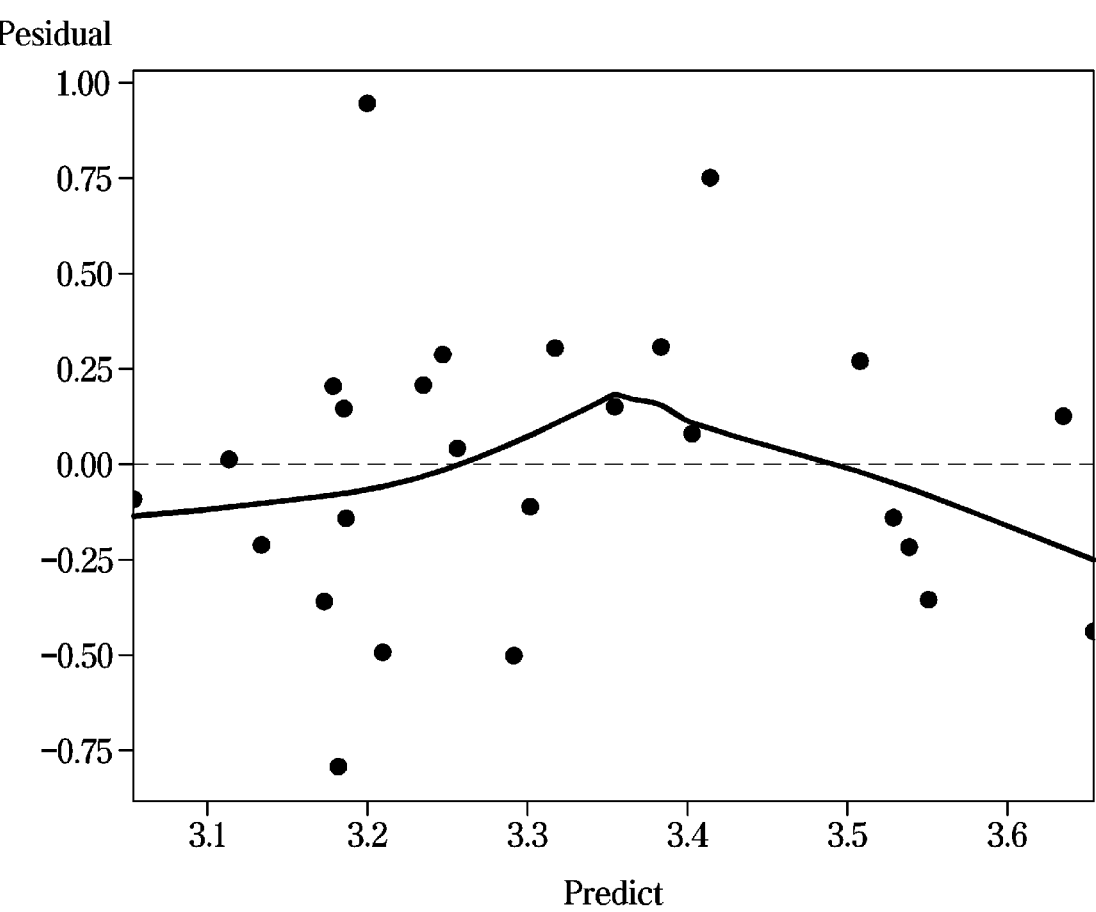
FIG. 19 is a table illustrating a comparison between predicted values and residuals for skin impedance measurements.
Figure 20:
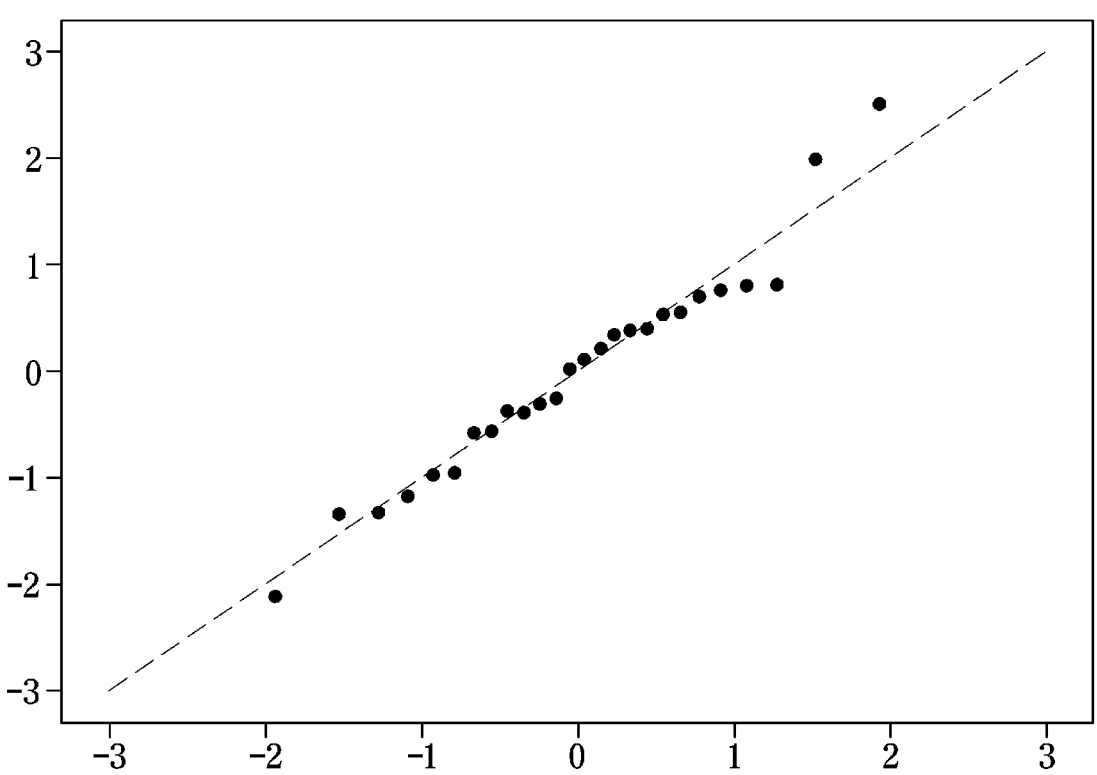
FIG. 20 is a graph illustrating a Q-Q plot of residuals for impedance measurements.
Figure 21:
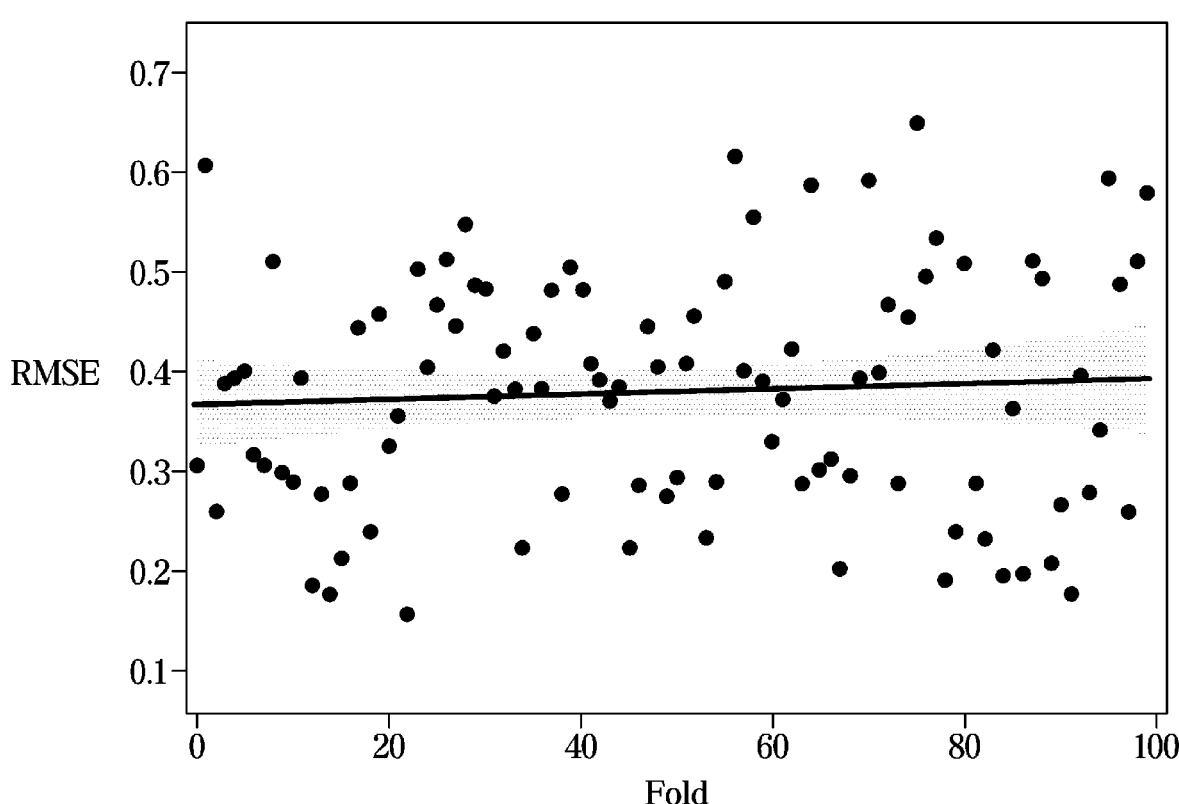
FIG. 21 is a graph illustrating root mean square errors for skin impedance values.

FIG. 17 is a table illustrating summary of regression model for skin impedance measurements. FIG. 18 is a table summarizing regression model coefficients for skin impedance measurements, FIG. 19 is a table illustrating a comparison between predicted values and residuals for skin impedance measurements, FIG. 20 is a graph illustrating a Q-Q plot of residuals for impedance measurements, and FIG. 21 is a graph illustrating root mean square errors for skin impedance values.

In FIGS. 17 to 21, by observing a change in a skin impedance of a forearm measured using an impedance device, a correlation between a bio-impedance and a vitamin D concentration in a body is analyzed, and an impedance measurement frequency that may be used to predict the vitamin D concentration level is identified.

From the normality tests, three impedance frequencies (21.1 Hz, 22.2 Hz, and 23.4 Hz) are found to satisfy the normality. In the disclosure, each of 21.1 Hz, 22.2 Hz, and 23.4 Hz is defined as a characteristic frequency.

In a model design, three frequencies identified in the normality test are set as input variables, and a log value of vitamin D concentration is set as output variables. Variable selection criteria are analyzed by defining significance levels as 0.05 and 0.1, respectively, when selecting and removing factors.

Referring to FIG. 17, the F statistic of the regression model shows a level of 4.543 at p=0.0435, and R2=0.159 for the regression formula, which shows an explanatory power of 15.9%.

In FIG. 18, analysis of the correlation between the collected frequency information and the vitamin D value confirms that the impedance measurement frequency of 21.1 Hz (t=2.131, p<0.05) appears to have a statistically significant effect.

As a result of comparing a predicted value (ŷ) and a residual (y-ŷ) to confirm the linearity of the model, it is observed that the predicted value (value) of vitamin D at 21.1 Hz shows a larger error at values less than 3.15, between 3.2 and 3.5, and greater than or equal to 3.65 (FIG. 19).

Shapiro-Wilk test performed to confirm the normality of the residuals shows that the normality is satisfied at a significance level of 5% with p=0.6285 (FIG. 20).

Statistical cross validation is performed by dividing all of the data into sub-data for training and validation (training: 80%, validation: 20%). An average root mean squared error (RMSE) and the standard deviation for 100 trials using random seeds are estimated to be 0.3789±0.1183 (FIG. 21).

As is apparent from the above description, an electronic apparatus may quickly and accurately measure a vitamin D concentration in a body by using a correlation for each characteristic frequency.

Meanwhile, the disclosed embodiments may be embodied in the form of a recording medium storing instructions executable by a computer. The instructions may be stored in the form of program code and, when executed by a processor, may generate a program module to perform the operations of the disclosed embodiments. The recording medium may be embodied as a computer-readable recording medium.

The computer-readable recording medium includes all kinds of recording media in which instructions which can be decoded by a computer are stored. For example, there may be a Read Only Memory (ROM), a Random Access Memory (RAM), a magnetic tape, a magnetic disk, a flash memory, and an optical data storage device.

Storage medium readable by machine, may be provided in the form of a non-transitory storage medium. "Non-transitory" means that the storage medium is a tangible device and does not contain a signal (e.g., electromagnetic wave), and this term includes a case in which data is semi-permanently stored in a storage medium and a case in which data is temporarily stored in a storage medium.

The method according to the various disclosed embodiments may be provided by being included in a computer program product. Computer program products may be traded between sellers and buyers as commodities. Computer program products are distributed in the form of a device-readable storage medium (e.g., compact disc read only memory (CD-ROM)), or are distributed directly or online (e.g., downloaded or uploaded) between two user devices (e.g., smartphones) through an application store (e.g., Play Store™). In the case of online distribution, at least a portion of the computer program product (e.g., downloadable app) may be temporarily stored or created temporarily in a device-readable storage medium such as the manufacturer's server, the application store's server, or the relay server's memory.

Although a few embodiments of the disclosure have been shown and described, it would be appreciated by those skilled in the art that changes may be made in these embodiments without departing from the principles and spirit of the disclosure, the scope of which is defined in the claims and their equivalents.

What is claimed is:

1. An electronic apparatus comprising:
an electrode sensor configured to apply a current to an object and to measure an impedance of the object;
a frequency controller configured to sequentially adjust a frequency of the current to a first characteristic frequency, a second characteristic frequency, and a third characteristic frequency;
a memory storing a plurality of correlations between respective impedances and corresponding vitamin D concentrations for each of the first characteristic frequency, the second characteristic frequency, and the third characteristic frequency; and
a processor configured to:
obtain, via the electrode sensor, a plurality of impedances of the object corresponding to the first characteristic frequency, the second characteristic frequency, and the third characteristic frequency,
calculate a first vitamin D concentration, a second vitamin D concentration, and a third vitamin D concentration based on the plurality of impedances and the plurality of correlations,
determine a difference value by subtracting the smallest vitamin D concentration among the first vitamin D concentration, the second vitamin D concentration and the third vitamin D concentration from the highest vitamin D concentration among the first vitamin D concentration, the second vitamin D concentration and the third vitamin D concentration, and
in response to the difference value being greater than a threshold value, calculate a composite vitamin D concentration based on the first vitamin D concentration, the second vitamin D concentration and the third vitamin D concentration.

2. The electronic apparatus of claim 1, wherein
the memory stores a parameter corresponding to biometric information related to the object, and
wherein the processor is further configured to calculate a final vitamin D concentration by applying the parameter to the composite vitamin D concentration.

3. The electronic apparatus of claim 1, wherein
the electrode sensor comprises a first electrode and a second electrode arranged on a rear surface of a main body of the electronic apparatus,
wherein the first electrode and the second electrode are in direct contact with the object, and
wherein the electrode sensor is further configured to apply the current through one of the first electrode or the second electrode and to measure a voltage between the first electrode and the second electrode so as to measure the impedance of the object.

4. The electronic apparatus of claim 2, wherein
the biometric information includes physical health information, and
wherein the physical health information includes at least one of gender, age, height, weight, body mass index (BMI), blood pressure level, white blood cell count, lipid level, liver level, or glucose level related to the object.

5. The electronic apparatus of claim 2, wherein
the biometric information includes a bio-signal measurement, and
wherein the bio-signal measurement includes at least one of skeletal muscle mass, body fat mass, body fat percentage, body mass index (BMI), body water, or basal metabolic rate.

6. The electronic apparatus of claim 2, wherein
the biometric information includes a blood analysis information, and
wherein the blood analysis information includes at least one of hemoglobin, fasting blood sugar, total cholesterol, high density lipoprotein cholesterol (HDL-cholesterol), triglyceride level, low density lipoprotein cholesterol (LDL-cholesterol), serum creatinine, Aspartate aminotransferase (AST), Alanine aminotransferase (ALT), or Gamma-glutamyl transpeptidase (y-GTP).

7. The electronic apparatus of claim 2, further comprising:
an input device configured to receive the biometric information from the object; and
a display,
wherein the processor is further configured to, based on the biometric information received through the input device, control the display to display the final vitamin D concentration.

8. The electronic apparatus of claim 7, wherein
the processor is further configured to, based on the final vitamin D concentration, control the display to provide a nutrition guide corresponding to the final vitamin D concentration.

9. The electronic apparatus of claim 1, wherein the first characteristic frequency is 21.1 Hz, the second characteristic frequency is 22.2 Hz, and the third characteristic frequency is 23.4 Hz.

10. The electronic apparatus of claim 1, wherein the processor is further configured to calculate a composite vitamin D concentration by averaging the first vitamin D concentration, the second vitamin D concentration and the third vitamin D concentration.

11. The electronic apparatus of claim 1, wherein the processor is further configured to calculate the composite vitamin D concentration by averaging two vitamin D concentrations that have the closest values among the first vitamin D concentration, the second vitamin D concentration and the third vitamin D concentration.

12. A control method of an electronic apparatus comprising an electrode sensor configured to apply a current to an object and to measure an impedance of the object, a frequency controller configured to adjust a frequency of the current and a memory storing a plurality of correlations between respective impedances and corresponding vitamin D concentrations for each of a first characteristic frequency, a second characteristic frequency, and a third characteristic frequency, the control method of the electronic apparatus comprising:

while a current is applied to the object, sequentially adjusting the frequency of the current to the first characteristic frequency, the second characteristic frequency, and the third characteristic frequency;

obtaining a plurality of impedances of the object corresponding to the first characteristic frequency, the second characteristic frequency, and the third characteristic frequency;

calculating the first vitamin D concentration, the second vitamin D concentration, and the third vitamin D concentration based on the plurality of impedances and the plurality of correlations, determining a difference value by subtracting the smallest vitamin D concentration among the first vitamin D concentration, the second vitamin D concentration and the third vitamin D concentration from the highest vitamin D concentration among the first vitamin D concentration, the second vitamin D concentration and the third vitamin D concentration, and in response to the difference value being greater than a threshold value, calculating a composite vitamin D concentration based on the first vitamin D concentration, the second vitamin D concentration and the third vitamin D concentration.

13. The control method of claim 12, further comprising calculating a final vitamin D concentration by applying a parameter to the composite vitamin D concentration, wherein the parameter corresponds to biometric information related to the object.

* * * * *